United States Patent [19]

Davidner et al.

[11] Patent Number: 5,104,373
[45] Date of Patent: Apr. 14, 1992

[54] METHOD AND APPARATUS FOR EXTRACORPOREAL BLOOD TREATMENT

[75] Inventors: Alan A. Davidner, Claremont; Henry V. Roohk; Max D. Lechtman, both of Westminster, all of Calif.

[73] Assignee: American Immuno Tech, Inc., Claremont, Calif.

[21] Appl. No.: 555,097

[22] Filed: Jul. 19, 1990

Related U.S. Application Data

[62] Division of Ser. No. 247,767, Sep. 22, 1988, Pat. No. 4,950,225.

[51] Int. Cl.$^5$ ............................................. A61M 37/00
[52] U.S. Cl. ................................................. 604/4; 604/5
[58] Field of Search ........................................... 604/4–6

[56] References Cited

U.S. PATENT DOCUMENTS

| | | | |
|---|---|---|---|
| 2,886,771 | 5/1959 | Vincent | 324/30 |
| 3,482,575 | 12/1969 | Claff et al. | 128/214 |
| 4,061,141 | 12/1977 | Hyden et al. | 128/214 R |
| 4,181,132 | 1/1980 | Parks | 128/399 |
| 4,191,182 | 3/1980 | Popovich et al. | 128/214 R |
| 4,321,918 | 3/1982 | Clark, II | 128/214 R |
| 4,322,275 | 3/1982 | Jain | 204/180 P |
| 4,381,004 | 4/1983 | Babb | 128/214 R |
| 4,479,798 | 10/1984 | Parks | 604/175 |
| 4,540,401 | 10/1985 | Marten | 604/28 |
| 4,563,170 | 1/1986 | Aigner | 604/5 |
| 4,576,143 | 3/1986 | Clark, III | 128/1 R |
| 4,692,138 | 9/1987 | Troutner et al. | 604/4 |
| 4,955,877 | 9/1990 | Shettigar | 604/4 X |

OTHER PUBLICATIONS

"Thermal Inactivation of Acquired Immunodeficiency Syndrome Virus, etc.", J. S. McDougal et al., *Journal of Clinical Investigation*, 76:875–877 (Aug. 1985).
"Inactivation of Lymphadenopathy–Associated Virus By Heat, etc.", by B. Spire, et al., *The Lancet*, 188–189, Jan. 26, 1985.
"The Effect of Nondamaging Intensity Laser Irradiation On the Immune System", by V. I. Kupin et al., *Neoplasma*, 34:3 325–330, 1987.
"The Destruction of Peripheral-Blood Lymphocytes By Extracorporeal Exposure to Ultraviolet Radiation", by A. Gunn et al., *Immunology*, 50:477–485 (Jun. 6, 1983).

Primary Examiner—Robert A. Hafer
Assistant Examiner—Kerry Owens
Attorney, Agent, or Firm—Stetina and Brunda

[57] ABSTRACT

Disclosed is a multimodal method and apparatus for extracorporeally treating certain blood borne infections, such as the infection of T-lymphocytes with the Human Immunodeficiency Virus. The method and apparatus of the invention includes (a) hyperthermic, (b) mechanical shear inducing, and (c) irradiation treatment modalities. These three treatment modalities may be carried out separately, in any order, or simultaneously, in any combination. The irradiation treatment mode preferably includes methods and means for subjecting at least a fraction of the blood to ultraviolet and/or x-ray and/or laser radiation. Before the blood is withdrawn from the human subject a chemical agent such as heparin may be administered to the subject for purposes of inducing lymphocyte migration from the lymph system into the circulatory system. Following extraction of a desired maximal volume of blood from the human subject, volume extenders may be mixed with the blood, thereby adjusting the extracorporeal blood volume as required or desired. Following completion of the extracorporeal treatment(s) the treated blood is returned to the patient.

4 Claims, 4 Drawing Sheets

METHOD AND APPARATUS FOR EXTRACORPOREAL BLOOD TREATMENT

This application is a division, of application Ser. No. 07/247,767, filed Sept. 22, 1988 now U.S. Pat. No. 4,950,225.

BACKGROUND OF THE INVENTION

This invention relates generally to a method and apparatus for extracorporeal blood treatment. More particularly, the invention provides a method and apparatus for treating certain disease states by way of an extracorporeal circuit capable of simultaneously and/or intermittently carrying out three separate treatment modalities.

The invention has particular utility in the treatment of human beings who have been infected with Human Immunodeficiency Virus-Type 1 (HIV-1) and will be discussed herein with particular reference thereto. HIV-1 has previously been known by several names including AIDS-related virus (ARV), Human T-Lymphotropic Virus-Type 3 (HTLV-3), and Lymphadenopathy-Associated Virus (LAV). The HIV-1 is associated with virtually all presently reported AIDS cases in the United States. It is noted, however, that a second HIV variant, know as Human Immunodeficiency Virus-Type 2 (HIV-2) has also been identified. HIV-2 shares similar biological properties with HIV-1 and is known to cause AIDS in certain regions of Central Africa. Thus, it is probable that the particular therapeutic efficacy of the present invention will extend to other AIDS-inducing viruses in addition to HIV-1 as well as to other immune disorders. Accordingly, as used herein, the term HIV-1 shall not be construed as a limiting or narrowing of the therapeutic applicability of the invention in any way.

A number of prior art devices are known for carrying out extracorporeal treatment of the blood. Indeed, many extracorporeal treatment methods have become well established as routine methods of treating specific conditions or diseases. Examples of extracorporeal treatment methods of known effectiveness include those adapted for extracorporeal blood oxygenation, plasmapheresis, leukapheresis, membrane dialysis, electrodialysis, radiotherapy, and extracorporeal treatment by various pharmacological and chemotherapeutic agents.

Specific examples of extracorporeal blood treatment devices and methods are described in U.S. Pat. Nos. 2,886,771 (Vincent); 4,321,918 (Clark II); 4,322,275 (Jain); 4,381,004 (Babb); 3,482,575 (Claff et al.); 4,479,798 (Parks); 4,540,401 (Marten); 4,563,170 (Aigner); 4,576,143 (Clark III); and 4,692,138 (Troutner et al.).

In particular, U.S. Pat. No. 3,482,575 (Claff et al.) discloses an extracorporeal blood oxygenation method where sodium bicarbonate is added to adjust the pH of the blood to 7.45–7.50 or higher prior to oxygenation. Such alkalization of the blood is purported to enable the blood to take up a greater amount of oxygen during the ensuing extracorporeal oxygenation process.

U.S. Pat. No. 4,692,138 (Troutner et al.) discloses a pump block which is used to interface an irradiation chamber with a roller pump. Such pump block is incorporated into an extracorporeal apparatus wherein photoactivatable agents are added to the patient's blood prior to extracorporeal irradiation of the blood. After such irradiation is completed, the blood is returned to the patient.

U.S. Pat. Nos. 4,321,918 and 4,576,143 (Clark II and Clark III) discloses a process and method of extracorporeally irradiating whole blood to alter lymphocyte function (Clark II) and to modify the immune response in humans affected with immune disorders (Clark III).

U.S. Pat. No. 4,479,798 (Parks) describes a subcutaneously implantable device for warming the blood so as to raise the patient's core temperature to 41.5°–42.5° C. for the purpose of hyperthermically retarding the growth of cancer cells within the body.

Also, U.S. Pat. No. 4,381,004 (Babb) describes a method for treating infectious and parasitic diseases whereby the patient's blood, or a fraction thereof, is treated extracorporeally with a biologically or pharmacologically active agent capable of inactivating the target microorganism. Thereafter, the inactivating agent is scavenged or removed from the blood prior to returning the blood to the patient. The Babb system is purported to allow the use of chemical or biological drugs which, at the doses required, would exhibit toxic or other adverse effects if administered directly to the patient.

Also, U.S. Pat. No. 4,540,401 (Marten) describes a means and method for removing immunoreactive compounds from blood using immunological homologes of the compound bound to the surfaces of lipid vesicles.

None of these extracorporeal methods and devices of the prior art have been specifically designed for the treatment of blood infected with the HIV-1. Given the present incurability of Acquired Immune Deficiency Syndrome (Aids) and the widely predicted capacity of the disease to reach widespread epidemic proportions, there exists a compelling need for a means of extracorporeally inhibiting or destroying the blood borne HIV-1 while preserving the physiological integrity and compatibility of the blood so that it may be returned to the patient following treatment. Thus, the present invention is intended to fill such compelling need.

The HIV-1 virus, like many retroviruses, is known to be temperature labile. In fact, the HIV-1 virus has been reported to undergo thermal inactivation in certain in vitro preparations at relatively moderate temperatures. McDougal, J. S. et al., Thermal Inactivation of Acquired Immunodeficiency Syndrome Virus, Human T-Lymphotropic Virus-III/Lymphadenopathy-Associated Virus, With Special Reference to Antihemophilic Factor, Journal of Clinical Investigation, 76:875–877 (August, 1985) and Spire, B et al., Inactivation of Lymphadenopathy-Associated Virus By Heat, Gamma Rays, and Ultraviolet Light; Lancet: 188–189 (Jan. 26, 1985).

Also, it is suspected tha T-lymphocytes which contain or have been infected by the HIV-1 virus may become structurally fragile. The possible fragility of HIV-1 infected cells suggests that such cells may be selectively disrupted or destroyed within an extracorporeal circuit by the induction of mechanical shear or be more sensitive to temperature and/or $PO_2$ increases or decreases or other physical agents described herein.

In addition, helium-neon and helium-cadmium laser irradiation, at certain wavelengths, has been reported to have certain immunostimulative and immunosuppressive effects on human lymphocytes in vitro. Kupin, V. I. et al., The Effect of Nondamaging Intensity Laser Irradiation on the Immune System, Neoplasma 34:3, 325–330 (1987). Other types of radiant energy within the electromagnetic spectrum are also known to have immunosuppressive/immunostimulative effects. Ultraviolet radiation has been reported to cause immunosuppresive effects which may prevent certain T-lymphocytes from being drawn to the HIV-1 virus. Horowitz, J., et al., Selective T Cell Killing of Human Lymphocytes by Ultraviolet Radiation; Cellular Immunology, 14:80–86 (1974). X-rays and other types of radiant energy may also have effects on the blood constituents and/or infecting organisms or viruses.

Thus, based on the present state of knowledge respecting the HIV-1 virus, applicant has identified firm scientific foundation for the provision of a novel, single extracorporeal device capable of intermittently or simultaneously utilizing (a) hyperthermia of the blood, (b) selective mechanical damage to virally affected cells, and (c) irradiation (preferably laser and/or UV and/or x-ray) as means of treating HIV-1 infected persons.

BRIEF SUMMARY OF THE INVENTION

In general, the present invention provides a method and apparatus for extracorporeally treating blood by any or all three treatment modalities. The three treatment modalities employed are:

(a) a means for hyperthermically treating the blood at a reduced pH under variable flow conditions;

(b) a means for mechanically damaging or lysing those blood cells which contain or have been affected by a virus, microorganism, or disease state; and (c) a means for subjecting whole blood or some fraction of the blood to irradiation (e.g. ultraviolet, visible, infrared, x-ray, laser, or radiofrequency radiation), and subsequently recombining and/or reinfusing such treated blood or blood fraction.

In accordance with one aspect of the invention there is provided an extracorporeal blood treatment device which is operative to adjust the temperature and pH of the blood be prescribed levels and to subsequently maintain such adjusted temperature and pH while holding the blood under static or low flow conditions for a period of time sufficient to bring about a desired therapeutic effect, such as deactivation of an infecting virus.

In accordance with another aspect of the invention the device will include means for extracorporeally separating and isolating selected blood cells, such as mononuclear leukocytes, and subjecting the isolated cells to selected types and doses of radiant energy (e.g. x-ray, UV, IR, visible, laser and/or radiofrequency) prior to recombining the treated cells with the remaining blood plasma and/or other formed elements.

In accordance with yet another aspect of the invention the device may include an extracorporeal recirculation loop wherein blood may be rapidly recirculated to create linear or other mechanical shear forces within the flowing blood. Such linear shear will cause selective disruption or damage to blood cells which are also being treated with hyperthermia reduced pH, etc. Specifically, T-lymphocytes which have been infected with the HIV-1 virus may be rendered fragile by the virus. By selectively disrupting or damaging such infected cells, an independent or adjuvant therapeutic effect may be achieved. Also, such mechanical forces may separate or detach viral particles or "buds" which may be attached to or extend from outer surfaces of certain blood cells.

In accordance with still another aspect of the invention, there is provided a means for optimizing the effectiveness of the extracorporeal blood treatment(s) by administering heparin to the patient prior to extraction of the blood into the extracorporeal treatment device of the invention. The heparin will be given at a dose sufficient to incduce or cause migration of lymphocytes from the lymph system into the circulatory system. Thus, the number of lymphocytes in the subsequently extracted blood will be increased, thereby rendering the extracorporeal treatment of certain lymphocyte-borne infections (e.g. HIV-1) more effective that it may otherwise have been.

A principal object of the invention is to provide an extracorporeal device capable of treating certain pathological conditions of the blood including but not limited to infections with the HIV-1 virus.

Another object of the invention is to provide a novel means of treating certain blood borne infections by holding the blood under variable and/or static-low flow conditions, at an elevated temperature and at a pH below 7.4, for a period of time sufficient to deactivate or destroy the infecting microorganism or virus without disturbing the physilogical functioning and compatibility of the blood.

A further object of the invention is to provide a novel method of treating certain blood borne infections by selectively damaging or disrupting cells which contain or have been affected by the infecting microorganism or virus.

An even further object of the invention is to provide a means for prospectively delaying or preventing the development of AIDS Related Complex and/or Acquired Immune Deficiency syndrome in individuals who have been infected with the HIV-1 virus but who are currently asymptomatic.

A still further object of the invention is to provide a means for periodically reducing the level of a virus or microorganism present in the blood of an infected individual so as to either fully irradicate the infecting virus/microorganism or maintain the virus/microorganism at subclinical levels.

A still further object of the invention is to provide a multi-purpose extracorporeal circuit or device capable of intermittently and/or simultaneously (a) carrying out hyperthermic treatment, (b) inducing mechanical shear, and/or (c) irradiating the blood.

An even further object of the invention is to provide a multipurpose extracorporeal circuit or device which includes means for initially separating and isolating selected blood cells and means for subsequently subjecting the isolated blood cells to specific types of radiant energy including, but not limited to, laser, ultraviolet, and/or x-ray radiation while optionally maintaining the temperature of the isolated cells within the range of approximately 41.5°–44.0° C.

Further objects and advantages of the invention will become apparent to those skilled in the art upon reading and understanding of the following detailed description and the accompanying drawings.

DETAILED DESCRIPTION OF A PREFERRED EMBODIMENT i. Methods

Figure 1:
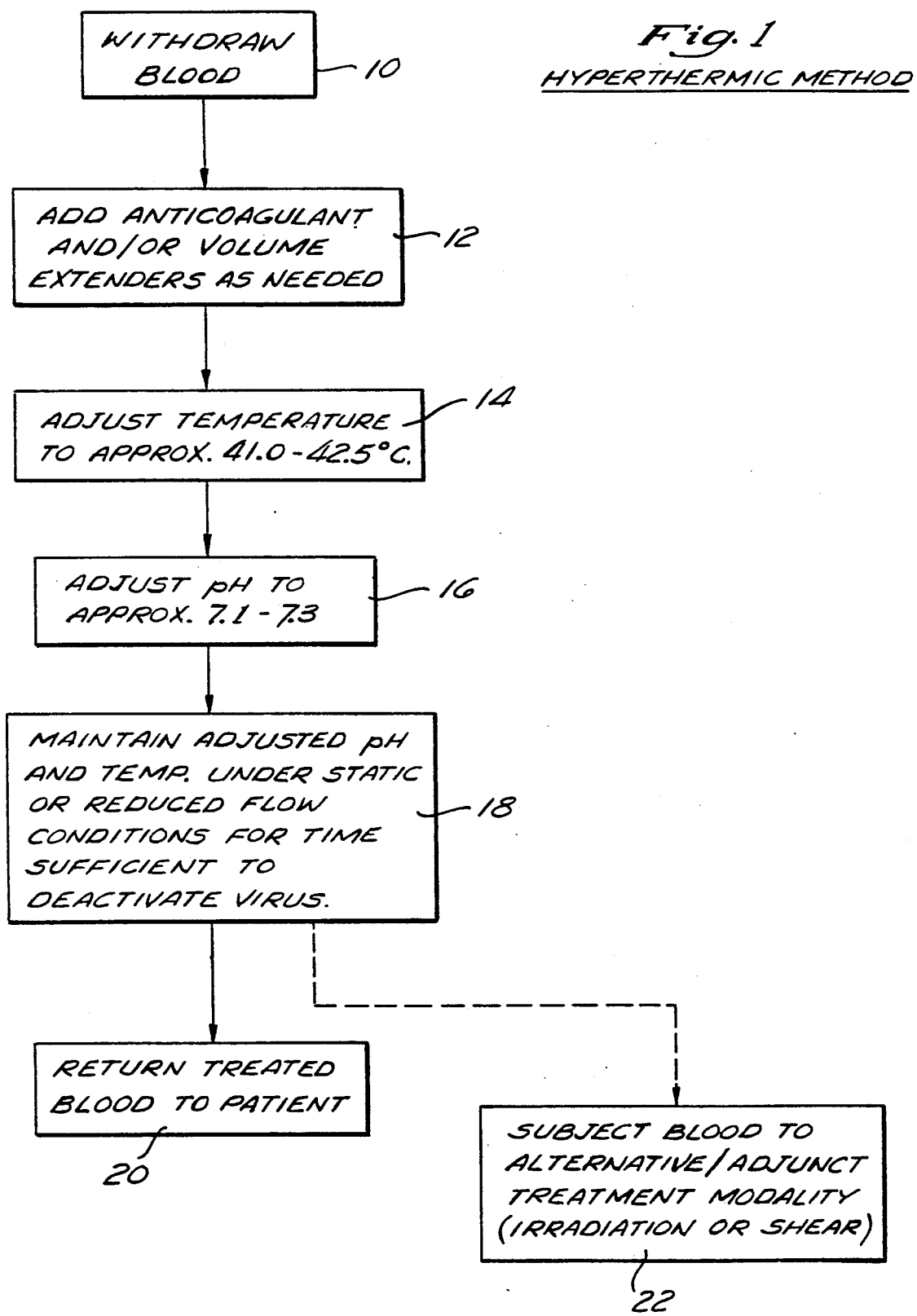
FIG. 1 is a flow diagram of a preferred method of hyperthermically treating blood in accordance with the invention.

Referring now to the drawings wherein the showings are for purposes of illustrating a preferred embodiment of the invention and not for purposes of limiting its scope, FIG. 1 outlines a method by which the present invention may be employed to cause thermal deactivation of the temperature labile HIV-1 virus.

As with any extracorporeal method, the initial step is to withdraw blood 10 from the patient. Such withdrawal of blood is generally accomplished by insertion of a single or double lumen cannula into a sizeable vein such as the femoral vein. As the blood is withdrawn, an anticoagulant (e.g. heparin, sodium citrate) is added 12 as needed. The addition of such anticoagulant prevents the blood from clotting in the extracorporeal circuit. Additionally, as a practical means of preventing clotting, the extracorporeal circuit may be primed by a small amount of heparinized saline solution prior to introduction of the blood. Of course, in instances where the human subject has been systemically treated with an anticoagulant drug prior to treatment, it may be unnecessary or even undesirable to add additional anticoagulant in the extracorporeal circuit.

The direct administration of heparin to the patient prior to withdrawal of the blood may have the effect of causing migration of lymphocytes from the lymph system into the circulatory system. See Janse, C. R. et al., Studies on Lymphocytes II: The Production of Lymphocytosis by Intravenous Heparin in Calves' Blood; 20:4, 443–52 (1962).

Following addition of the desired anticoagulant and/or extender, the temperature of the blood is adjusted 14 to 41.0°–42.5° C. Since normal human body temperature is 37° C., the transition to the adjusted temperature of 41.0°–42.5° C. will generally require that the blood be gently warmed. Such warming of the blood is accomplished by providing a coil-type blood warmer within the extracorporeal circuit and slowly recirculating the blood through the warmer until the desired temperature has been reached.

After the temperature of the blood has been adjusted to the desired 41.0°–42.5° C., the pH of the blood (as measured at the elevated temperature) will be adjusted to 7.2+/−0.1. Such adjustment of pH is generally accomplished by raising the $pCO_2$ of the blood through the use of an extracorporeal oxygenator within the extracorporeal system. Such oxygenator may also be employed to adjust and control the $PO_2$ of the extracorporally circulating blood as certain effects of UV radiation are known to be significantly altered under hyperoxic conditions. Also, sodium bicarbonate may be periodically added to the circulating blood to bring about increases in pH when necessary.

Examples of commercially available blood oxygenators which may be used in connection with the extracorporeal treatment device and method of the present invention include:

Oxygenators

Baxter Bentley Laboratories
17502 Armstrong Avenue
Irvine, Calif. 92714
CM-40 Hollow Fiber Oxygenator Scimed Life Systems
13000 Country Road 6
Minneapolis, Minn. 55441
0800-24 Membrane Oxygenator Medtronic Cardiopulmonary
4633 East La Palma
Anaheim, Calif. 92807
Model 1380 Hollow Fiber Oxygenator Bard Cardiosurgery
P. O. Box M
Concord Road
Billerica, Mass. 01821
HF-4000 Hollow Fiber Oxygenator Simko Medical Instruments Manufacturing Co., Ltd
3-23-13, Hongo
Bunkyou-Ky
Tokyo, Japan 113
Mera-Silox Model 0800

During the extracorporeal treatment the blood is preferably maintained at such adjusted pH and temperature under static or very slow flow conditions 18. Ideally, such static or reduced flow conditions will be accomplished by slowly circulating the blood through a capacitance reservoir positioned within the extracorporeal circuit. Such reservoir will be sufficiently large, and the flow rate of blood into and out of the reservoir will be sufficiently low, that the blood will be permitted to reside within the capacitance reservoir under substantially static conditions. Such static or reduced flow condition, as well as the adjusted pH and temperature, will be maintained for a period of time sufficient to deactivate all or a portion of the HIV-1 virus present in the blood. In this presently preferred embodiment, such hyperthermic treatment conditions will be maintained for approximately 60 to 240 minutes.

After the virus has been inhibited, the blood may be returned 20 to the patient or shunted to a separate region of the extracorporeal device where it may be subjected to an alternative/adjunct treatment modality 22.

Figure 2:
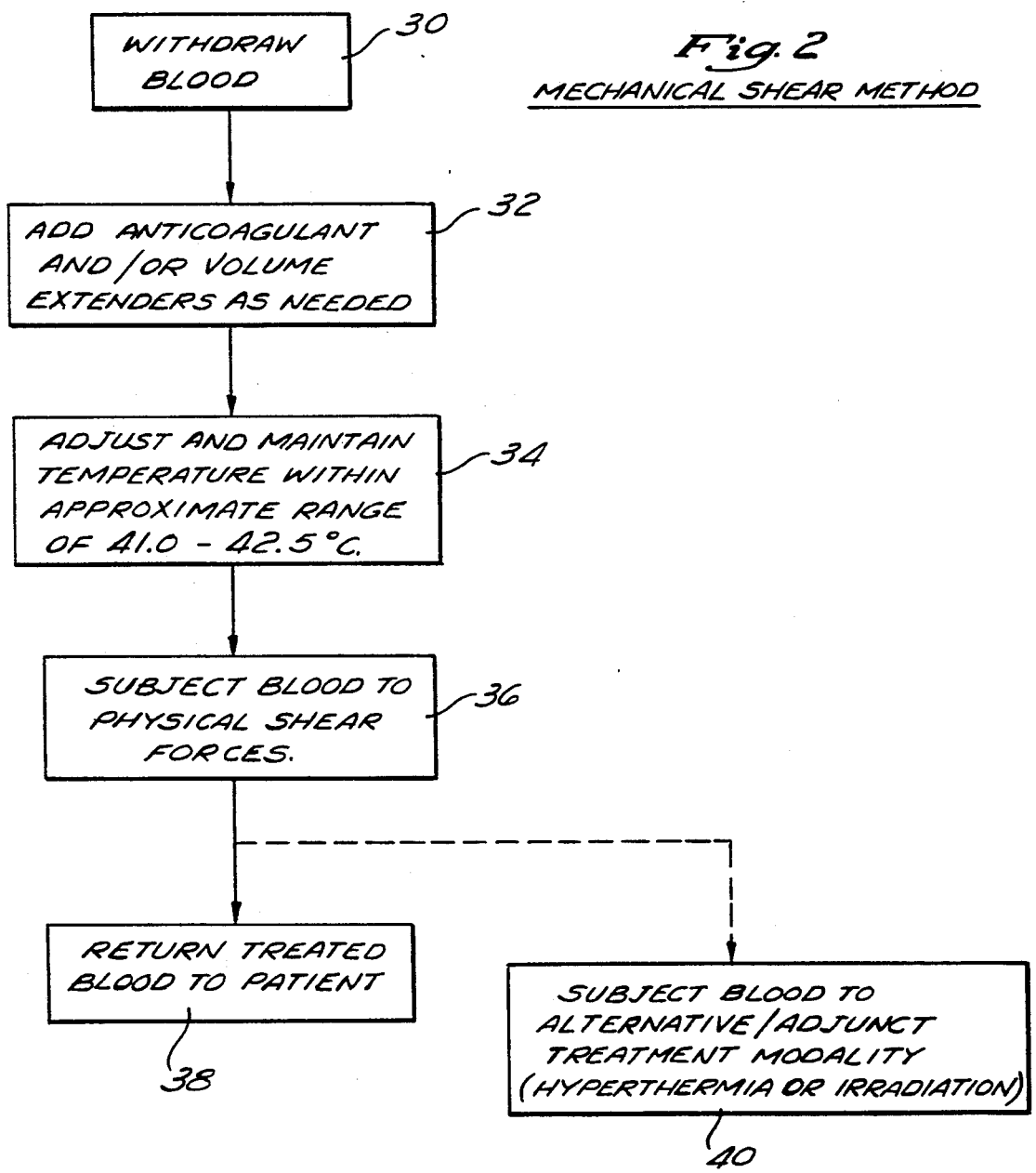
FIG. 2 is a flow diagram of a preferred method of subjecting blood to physical shear in accordance with the present invention.

One of the alternative/adjunct treatment modalities provided by the present invention is the induction of "mechanical shear" within the extracorporeal circuit, as outlined in the block diagram of FIG. 2. Referring to FIG. 2, blood is initially withdrawn from the vein 30 or received from another portion of the extracorporeal circuit wherein the blood had previously been treated. If freshly withdrawn blood is being used, anticoagulant will be added 32 as described previously. If, however, the blood has already been subjected to treatment in another portion of the extracorporeal circuit, it will have already received anticoagulant and in all probability will not require further anticoagulant addition. Inert blood extenders may also be added as needed to minimize the volume of blood extracted from the patient and/or to maintain optimal functioning of the extracorporeal treatment device.

The temperature of the blood is adjusted and maintained 34 within the approximate range of 41.0°–42.5° C.

The blood is then recirculated rapidly in a tubular recirculation loop so as to induce linear shear 36 within the circulating blood. Such linear shear will be induced for the purpose of mechanically damaging those blood cells which may have been rendered fragile due to infection. Also, such physical forces will serve to break or interrupt the attachment of viral particles to the surfaces of blood cells.

The induction of mechanical shear 36 is preferably accomplished by passing the blood through a tube at a relatively high flow rate. The result is that a frictional interaction will occur between the flowing blood and the inner wall of the tubing. Such frictional interaction will induce the desired linear shear forces within the circulating blood.

During this mechanical shear treatment, the temperature of the blood may be maintained at an elevated level, such as approximately 41.0°–42.5° C.

After the blood has been subjected to shear 36 for a period of time sufficient to destroy or disrupt the fragile infected blood cells and/or to separate viral particles from the outer surfaces of blood cells, the blood may be (a) returned 38 to the patient or (b) shunted to another area of the extracorporeal device 40 for purposes of carrying out another alternative/adjunct treatment modality.

Figure 3:
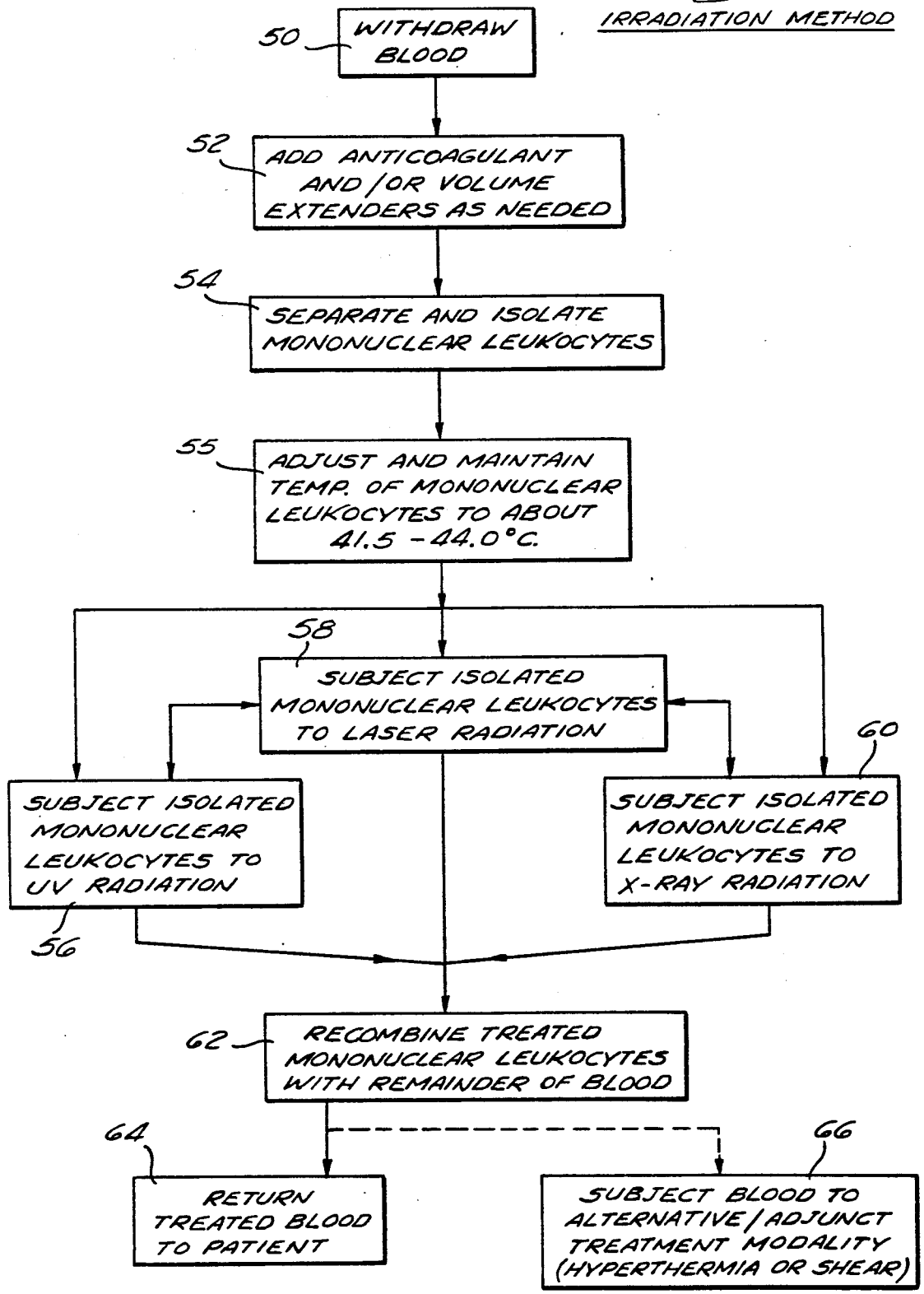
FIG. 3 is a flow diagram of a preferred method of subjecting blood to x-ray and/or UV and/or laser irradiation in accordance with the present invention.

The third alternative/adjunct treatment method of the present invention is the irradiation (x-ray and/or laser and/or UV) method outlined in the block diagram of FIG. 3. Again, blood is withdrawn 50 or obtained from another region of the extracorporeal circuit and anticoagulant and/or volume extenders are added 52 as needed.

The blood is then subjected to a process whereby selected cells are separated and isolated 54. Such may be achieved by simple centrifugation or by the positioning of a blood cell separator within the extracorporeal circuit. Depending upon the centrifugation and/or pheresis techniques employed, specific cell types may be separated from the remaining plasma and other formed elements of the blood. For example, leukocytes in general may be separated from the red cells and plasma of the blood. Or, more definitively, mononuclear leukocytes in particular may be separated and isolated. Examples of commercially available pheresis systems which may be employed in connection with the extracorporeal treatment method/device include: IBM 2997 Blood Cell Separator and Buffer System, Cobe Laboratories, 1185 Oak Street, Lakewood, Colo. 80215; Model 30, 30S Cell Separator, Haemonetics Corporation, 400 Wood Road, Braintree, Mass. 02184; Model CS-3006, Fenwal Division, Baxter Health Care Corp., Santa Ana, Calif.

Alternatively, standard centrifugation techniques may be employed to separate and isolate the desired cell types.

Regardless of the specificity of the separation method 54 employed, the isolated cells may be subjected to any or all of three preferred radiation treatments such as ultraviolet radiation 56 for the purpose of inhibiting T-lymphocytes and/or specific types of laser radiation 58 for the dual purposes of inhibiting T-lymphocytes and/or immunostimulation or stimulation of certain cell types and/or x-ray radiation 60 may also be used. Additionally, the temperature of the blood may be adjusted and controlled within the range of 41.5°–44.0° C. during these irradiation treatments to optimize the effects thereof.

After the isolated blood cells have been subjected to the desired ultraviolet 56 and/or laser 58 and; or x-ray 60 irradiation, the cells may be recombined 62 with the previously separated plasma and other formed elements of the blood. Alternatively, the treated cells may be independently suspended in plasma or any suitable suspending agent which will permit reinfusion or fluidic transfer of the cells.

Following recombination or suspension 60 the treated cells will be returned 64 to the patient or shunted to another area of the extracorporeal circuit where they will be subjected to an alternative/adjunct treatment modality 66.

ii Device

Figure 4:
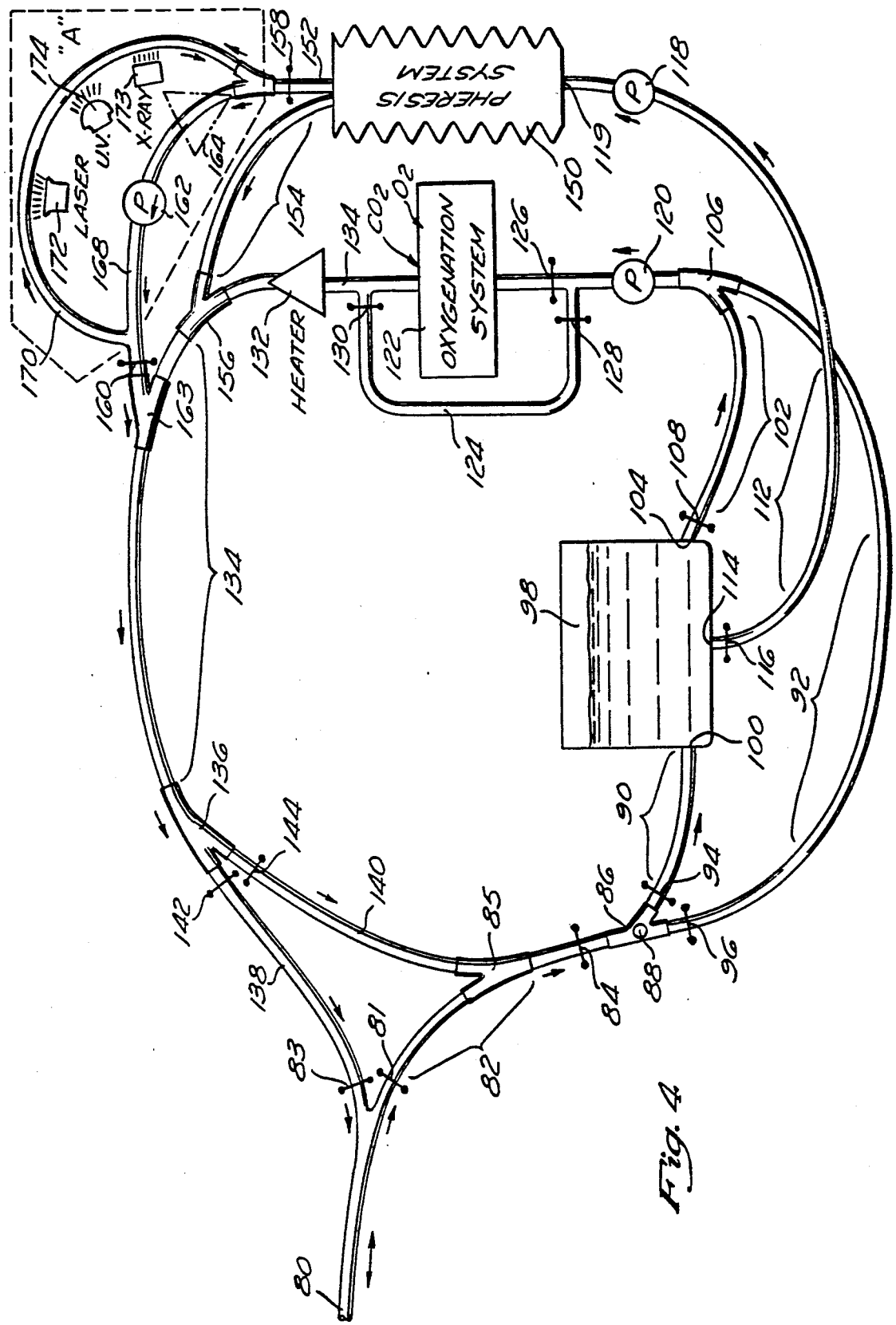
FIG. 4 is a schematic diagram of a preferred extracorporeal blood treatment apparatus of the present invention.

A preferred multimodal extracorporeal circuit whereby each of the three previously outlined treatment methods may be separately and/or simultaneously performed is shown in FIG. 4. A single lumen cannula 80 is inserted into a relatively large vein of the patient, such as the femoral vein. Initially, blood is withdrawn through the cannula lumen 80 into venous drainage line 82. A venous drainage clamp 84 is positioned within venous drainage line 82 so as to permit stoppage of the blood flow from the patient as desired. A Y-adaptor 86 is positioned at one end of venous drainage line 82. The Y-adaptor 86 is provided with a latex injection port 88 through which heparin or any other anticoagulant may be introduced.

The presence of Y-adaptor 86 at the base of the venous drainage line 82 further serves to bifurcate line 82 into a reservoir supply line 90 and an oxygenator feedline 92. Clamp 94, when closed, will cause the incoming blood to be passed through the oxygenator feedline 92. Alternatively, closure of clamp 96 and opening of clamp 94 will cause the incoming blood to be directed through the reservoir supply line 90 and subsequently into the reservoir 98 through inlet port 100.

A first reservoir outlet line 102 exits the reservoir through a first outlet port 104. The first outlet line 102 converges with oxygenator feedline 92 at Y-adaptor 106. Clamp 108, when opened, permits free outflow of blood from the reservoir 98 through outlet line 102 and into oxygenator feedline 92 via Y-connector 106.

Alternatively, a second reservoir outlet line 112 exits the reservoir 98 through second outlet port 114 and serves to connect the reservoir 98 to the inlet 119 of pheresis system 150.

Blood flowing out of reservoir 98 through exit port 104 and through outlet line 102, or alternatively blood received through venous drainage line 82 and subsequently directed through oxygenator supply line 92 will be moved by pump 120 in the direction indicated by the arrow within the pump symbol. The pump 120 is a standard roller pump of the type used in combination with commercially available oxygenation systems (examples listed above). The pump 120 feeds blood into the membrane oxygenation system 122, or alternatively through a membrane oxygenation system bypass loop 124 depending on the relative opening and closing of clamps 126, 128, and 130. An inline blood heater 132 may be incorporated into or positioned outside of the extracorporeal membrane oxygenation unit. The blood heater 132 is preferably positioned on the oxygenator outlet line 134. The oxygenator outlet line 134 extends in a loop-like fashion to a Y-connector 136 whereby line 134 bifurcates to form (a) a patient return segment 138 and (b) an extracorporeal recirculation segment 140. Accordingly, the opening and/or closing of clamps 142 and 144 will determine whether blood flowing through oxygenator outlet line 134 is to be returned to the patient via segment 138 or shunted back into the extracorporeal circuit via segment 140.

Blood which exits the reservoir 98 through second exit port 114 and pheresis system supply line 112 will be pumped through pump 118 into a pheresis system 150 capable of effecting separation of mononuclear leukocytes from the plasma and remaining formed elements of the blood. Pheresis systems of the type used herein are commercially available (examples listed above).

After the separation of the blood has been accomplished, the leukocytes will be suspended in a suitable extending agent such as blood plasma or anticoagulant citrate dextrose adenine (ACDA), and will pass through leukocyte separation line 152. The remaining plasma and formed elements of the blood will pass through extracorporeal return line 154. The plasma and formed elements passing through return line 154 will enter the membrane oxygenation system outlet line 134 via Y-connector 156 so as to be reintroduced into the mass of whole blood within the extracorporeal system. The separated leukocytes on the other hand will pass from the leukocyte separation line 152 into a leukocyte isolation and treatment loop circled by dotted lines and labeled "A". The suspended leukocytes may be held within isolation and treatment loop A by closing clamps 158 and 160. Thereafter pump 162 may be utilized to continually recirculate the suspended leukocytes within the isolation loop A which is formed generally of lines 168 and 170. A standard roller pump 162 is positioned on line 168 so as to permit controlled recirculation of the suspended leukocytes around loop A in the manner indicated by the solid arrows.

An optional heater 164 is also positioned in line 168 so as to provide for temperature control of the suspended leukocytes within the leukocyte treatment loop A.

A laser irradiation head 172 is positioned so as to emit laser energy into the suspended leukocytes flowing through line 170. The laser device through which such energy is emitted is preferably a Gallium-Arsinide, helium-cadmium, helium-neon or argon type laser, emitting energy at 90.4 nm, 441.6 nm, 633 nm, or other wavelengths which are found to have desired effects.

Also, an ultraviolet light source 174 is positioned so as to emit ultraviolet energy into the suspended mononuclear leukocytes passing through line 170. The ultraviolet light source 174 is preferably of the type described by Gunn, A. et al., in: The Destruction of Peripheral-Blood Lymphocytes by Extracorporeal Exposure To Ultraviolet Radiation; Immunology 50:477–485 (1983) (e.g. transparent plastic tubes capable of emitting shortwave UVC radiation at a wavelength of 254 nm).

Additionally, an x-ray source 173 may be positioned within the extracorporeal circuit to subject the circulating leukocytes to the effects of x-ray radiation.

After the treatment of the leukocytes in loop A has been completed, the loop may be drained by opening clamp 160 and releasing the suspended leukocytes into the oxygenator outlet line 134 through Y-connector 163. Thus, the treated/irradiated mononuclear leukocytes are returned to the main extracorporeal loop wherein they may undergo further treatment(s) or be returned to the patient.

Any excess, physiologically incompatible, or undesired volume of extending agents which may have been added to the blood in the extracorporeal circuit may be separated and removed, wholly or in part, prior to returning the treated blood and/or blood cells to the patient.

MULTIMODAL OPERATION OF THE PREFERRED EMBODIMENT

Extracorporeal Apparatus

The extracorporeal apparatus diagrammed in FIG. 4 is operative to separately and/or simultaneously effect one or more of the treatment methods described in FIGS. 1-3. The manner in which such multimodal treatment is carried out may be most easily appreciated by referring directly to FIG. 4 in accordance with the following operative description.

Referring to FIG. 4, clamps 81 and 83 are initially open to permit drainage of blood from the cannula lumen 80 into the venous drainage line 82. Clamps 84 and 94 are initially opened and clamp 96 is initially closed to permit the freshly withdrawn blood to immediately enter the extracorporeal reservoir from which it can be pumped to oxygenation system supply line 92 through the angled segment of Y-connector 86 and to heater 132 through line 134. A desired amount of heparin may be added through injection port 88 to effect or maintain anticoagulation of the blood within the extracorporeal circuit. Roller pump 120 is energized and set at a slow flow rate to slowly pump the blood into the extracorporeal device as it is withdrawn from the patient.

After a sufficient amount of blood has been accumulated, the multimodal extracorporeal treatment will be begun. Extending agents may be added as needed to adjust the blood volume within the extracorporeal circuit and to avoid excessive extraction of blood from the patient. As described herein, the device of the present invention is designed to carry out up to three separate modes of treatment. Such treatment modalities may be conducted separately or concurrently. However, in order to limit the volume of blood required within the extracorporeal circuit at any given point in time, it is generally preferable to conduct the (a) hyperthermic, (b) mechanical shear, and (c) UV/laser/x-ray irradiation treatments separately but consecutively.

The device of the present invention is capable of conducting the three separate treatments simultaneously and/or separately in any order. However, for purposes of simplicity and description, each of the three treatment modalities will be separately described herein. Accordingly, for the purposes of this description, the operative aspects of the "mechanical shear" treatment will be described first, followed by the "hyperthermic" and "irradiation" treatments.

i. Mechanical Shear Treatment

The induction of mechanical shear is accomplished by opening clamps 84, 96, 128, 130, and 144 while closing clamps 126, 160, and 142. Pump 120 is adjusted to a relatively high flow rate of approximately 500–1500 ml/min through the 0.25 inch IV tubing such that the blood will be continually recirculated through the membrane oxygenation bypass loop 124, and through lines 134, 140, and 92 in a repetitive, generally circuitous motion. Such recirculation of the blood will result in continuous frictional interaction between the flowing blood and the inner wall of the tubing. Such frictional interaction will create sufficient linear shear to disrupt some or all of the infected cells and/or to separate viral particles from host cells or potential host cells. This continuous recirculation of the blood will continue for a period of 60-240 minutes.

Generally this mechanical shear treatment will be performed while the temperature of the blood is held within an elevated temperature range, such as approximately 41.0°-42.5° C.

ii. Hyperthermic Treatment

In accordance with the hyperthermic treatment mode of the present invention, the temperature of the recir120 to 41.0°-42.5° C. Thereafter, the oxygenator bypass loop 124 will be eliminated by closing clamps 128 and 130 while opening clamp 126. The recirculating blood will then be passed directly through the oxygenator 122 wherein the $pCO_2$ of the blood will be increased or decreased as required to achieve a pH of 7.2+/−0.1 at the elevated temperature.

When the pH and temperature of the recirculating blood has stabilized, clamps 94 and 108 will be opened and clamps 96 and 116 will be closed. As a result, the temperature/pH adjusted blood will flow into reservoir 98.

Additional blood may be drawn into the system and treated in accordance with the above method until the volume of blood within the extracorporeal system reaches approximately 0.15-1.0 L, depending upon the size and condition of the human subject.

Thereafter, clamp 108 is opened and the flow rate or blood through the oxygenator is reduced to approximately 200 ml/min. At such flow rate into and out of reservoir 98, the condition of blood within the reservoir 98 at any given point in time will be nearly static. Nonetheless, even such reduced flow rate will be sufficient to enable maintenance of the desired temperature and pH.

Preferably, such conditions will be maintained for a period of approximately 60-240 minutes.

iii. Irradiation Treatment

The third treatment modality which is accomplished by the device shown in FIG. 4 is the treatment of white blood cells or, even more specifically, mononuclear leukocytes, by x-ray and/or laser and/or UV radiation. Such is accomplished by opening clamp 116 permitting blood to drain from reservoir 98 through secondary outlet port 114 and into the pheresis system supply line 112. The pump 118 will supply the blood to a commercial pheresis system 150 which is used to accomplish separation of selected blood cells (mononuclear leukocytes) from the remaining blood. The remainder of the blood is then passed through return line 154 into the oxygenation system outlet line 134 and may be directly returned to the patient by closing clamp 144 and opening clamps 142 and 83, thereby permitting the plasma, red blood cells, and other elements of the blood to flow through the cannula lumen 80 back into the patient.

The separated and isolated mononuclear leukocytes are suspended in blood plasma or some other suitable suspending agent and are passed from the pheresis system 150 into the mononuclear leukocyte recirculation loop A. After the loop A has been filled with suspended mononuclear leukocytes cells, clamps 152 and 160 are closed and pump 162 is energized so as to continually slowly recirculate the suspended white cells through lines 168 and 70 in a loop-like fashion. An optimal heater 164 is provided such that the desired temperature of the suspended white cells may be maintained or increased during treatment. The circulating mononuclear leukocytes may be held within the temperature range of 41.5°-44.0° C. while the irradiation treatment(s) are carried out. Such elevated temperature in conjunction with the irradiation treatments will optimize the therapeutic effectiveness of the devices.

A laser source 172 may be used to direct two types of laser energy into the circulating mononuclear leukocytes as they flow through line 170. In this preferred embodiment, the slowly circulating mononuclear leukocytes may be subjected to one laser treatment to effect immunostimulation (such as 633 nm) and another to effect immuno-suspension (such as 441.6 or 904.0 nm). Other wavelengths may, of course, be employed as well.

Also an ultraviolet light source 174 is positioned so as to emit ultraviolet radiation into the circulating mononuclear leukocytes in line 170. The emission of ultraviolet radiation from light source 174 will be of sufficient intensity to selectively inhibit T lymphocytes or particularly infected mononuclear leukocytes. Such ultraviolet irradiation of the circulating white blood cells will be maintained for a period of 60-240 min.

An x-ray source 173 is also positioned within the irradiation loop so as to emit x-ray radiation into the circulating mononuclear leukocytes.

After the laser and/or ultraviolet and/or x-ray irradiation of the suspended white cells is completed, the cells are returned to the patient by opening valve 160 and permitting the suspended mononuclear leukocytes cells to flow through lines 134, 138, and 80 back into the venous circulation.

Alternatively, the previously separated red cells, plasma, and other formed elements of the blood may be initially shunted into the reservoir 98 by way of the main circuit. Thereafter, upon completion of the laser and/or ultraviolet and/or x-ray mononuclear leukocytes, such irradiation of the cells may be also be sent into reservoir 98 by way of the main circuit thereby recombining the separated mononuclear leukocytes with the remainder of the blood. The reconstituted blood may then be recirculated through the membrane oxygenation system and heater, may be subjected to physical shear within the above-described shear during recirculation loop, or may returned to the patient as reconstituted whole blood.

The three separate treatment modalities of the present invention may be employed singularly in any other or simultaneously in any combination. The order and use of each of the three separate treatment modalities will be determined by the treating physician and/or perfusionist on the basis of the desired therapeutic effects and various technical factors which may be present.

Although the methods and apparatus of the present invention have been described herein with reference to specifically preferred embodiments, it must be appreciated that various modifications and alterations may be made without departing from the spirit and scope of the invention. Accordingly, it is intended to include all such modifications and alterations within the scope of the appended claims and the equivalents thereof.

What is claimed is:

1. A method for extracorporeal hyperthermic treatment of blood, said method comprising the steps of:

withdrawing a quantity of blood from a human subject;

extracorporeally adjusting the temperature of said quantity of blood to 41.0°–42.5° C.;

extracorporeally adjusting the pH of said quantity of blood to 7.2+/−0.1 at 41.0°–42.5° C.;

maintaining said quantity of blood at the adjusted temperature of 41.0°–42.5° C. and at the adjusted pH of 7.2+/−0.1 under low flow conditions for a period of time sufficient to accomplish the desired therapeutic effect; and reinfusing said quantity of blood into the human subject.

2. The method of claim 1 further comprising the step of administering at least one chemical agent operative to cause migration of lymphocytes into the circulatory system of the human subject prior to said withdrawal of a quantity of blood therefrom.

3. The method of claim 2 wherein the chemical agent comprises a pharmaceutically acceptable preparation of heparin.

4. The method of claim 2 further comprising the addition of at least one volume extending agent to adjust the extracorporeal blood volume following withdrawal thereof from the human subject.

* * * * *